United States Patent [19]

Waterhouse et al.

[11] Patent Number: 5,164,503

[45] Date of Patent: Nov. 17, 1992

[54] PREPARATION OF AMINOCYCLOPENTANE ACIDS

[75] Inventors: Ian Waterhouse, Royston; David R. Marshall, Hertford; Eric W. Collington, Welwyn; Christopher J. Wallis, Royston; Peter Hallett, Bassingbourn, all of England

[73] Assignee: Glaxo Group Limited, London, England

[21] Appl. No.: 698,895

[22] Filed: May 13, 1991

Related U.S. Application Data

[63] Continuation of Ser. No. 402,514, Sep. 5, 1989, abandoned, which is a continuation of Ser. No. 122,638, Nov. 10, 1987, abandoned, which is a continuation of Ser. No. 874,830, Jun. 16, 1986, abandoned, which is a continuation of Ser. No. 546,049, Oct. 27, 1983, abandoned.

[30] Foreign Application Priority Data

Oct. 28, 1982 [GB] United Kingdom ............... 8230770

[51] Int. Cl.[5] ............... C07D 275/00; A61K 31/241
[52] U.S. Cl. ............... 546/239; 548/572; 544/171; 544/399; 544/59; 544/58.2; 540/544; 540/553; 540/575; 540/612
[58] Field of Search ............... 546/238, 239; 544/171, 544/399, 59, 58.2; 548/572; 540/544, 553, 575, 612

[56] References Cited

U.S. PATENT DOCUMENTS 4,342,756 8/1982 Collington et al. ............... 546/234

OTHER PUBLICATIONS

McOmie Protective groups in Organic Chemistry p. 183, pp. 205-211 1973.

*Primary Examiner*—Jane T. Fan
*Attorney, Agent, or Firm*—Bacon & Thomas

[57] ABSTRACT

A process is described for the preparation of compounds of the formula

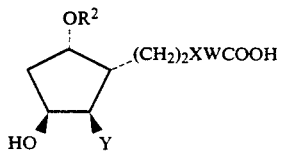

in which
W is $C_{1-7}$ alkylene
X is cis or trans —CH=CH— or —$CH_2Ch_2$—
Y is a saturated heterocyclic amino group, and
$R^2$ is substituted or unsubstituted phenyl-, thienyl- or naphthyl-alkyl, or cinnamyl,
and their salts and solvates.

The process comprises hydrolysing a corresponding ester, amide, nitrile or ortho-ester. The starting materials are preferably prepared by reducing the corresponding cyclopentanone and hydrolysis can take place simultaneously with reduction.

18 Claims, No Drawings

PREPARATION OF AMINOCYCLOPENTANE ACIDS

This application is a continuation of application Ser. No. 07/402,514, filed Sep. 5, 1989, now abandoned, which is a continuation of application Ser. No. 07/122,638, filed Nov. 10, 1987, now abandoned, which is a continuation of application Ser. No. 06/874,830, filed Jun. 16, 1986, now abandoned, which is a continuation of application Ser. No. 06/546,049, filed Oct. 27, 1983, now abandoned.

This invention concerns the preparation of aminocyclopentane acids and particularly the preparation of β-hydroxy compounds of the general formula (1)

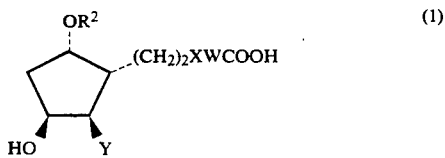

wherein

W is straight or branched $C_{1-7}$ alkylene;

X is cis or trans —CH=CH— or —CH$_2$CH$_2$—;

Y is a saturated heterocyclic amino group (attached to the cyclopentane ring via the nitrogen atom) which has 5-8 ring members and (a) optionally contains in the ring —O—, —S—, —SO$_2$—, or —NR$^3$ (where R$^3$ is a hydrogen atom, $C_{1-7}$ alkyl or aralkyl having a $C_{1-4}$ alkyl portion); and/or (b) is optionally substituted by one or more $C_{1-4}$ alkyl groups; and R$^2$ is (i) straight or branched $C_{1-5}$ alkyl substituted by (a) phenyl [optionally substituted by $C_{1-6}$ alkyl, $C_{5-7}$ cycloalkyl, phenyl (optionally substituted by $C_{1-4}$ alkyl, $C_{1-4}$ alkoxy or phenyl)], (b) thienyl [optionally substituted by $C_{1-6}$ alkyl, $C_{1-6}$ alkoxy, $C_{5-7}$ cycloalkyl or phenyl (optionally substituted by $C_{1-3}$ alkyl, $C_{1-3}$ alkoxy or halogen)], or (c) naphthyl (optionally substituted by $C_{1-4}$ alkyl or $C_{1-4}$ alkoxy), or (ii) cinnamyl and the physiologically acceptable salts and solvates (e.g. hydrates) thereof.

The structural formulae herein are to be understood to include the enantiomers of each of the compounds concerned as well as mixtures of the enantiomers including racemates, even though the precise structure as set out only relates to one enantiomer.

The compounds of formula (1) are described in British Patent Specification 2097397A. They have shown endoperoxide and thromboxane antagonist activity and are therefore of interest in the treatment of asthma and cardiovascular diseases.

The process of the invention is particularly applicable to the preparation of compounds of formula (1) as defined below.

The amino group Y enables the compounds of formula (1) to form salts with inorganic or organic acids, e.g. hydrochlorides and maleates. Salts may also be formed with bases, and examples of such salts are alkali metal (e.g. sodium or potassium), alkaline earth metal (e.g. calcium or magnesium), ammonium, substituted ammonium (e.g. tromethamine or dimethylaminoethanol), piperazine, N,N-dimethylpiperazine, morpholine, piperidine and tertiary amino (e.g. trimethylamine) salts.

The heterocyclic amino group Y may for example have a 5,6 or 7-membered ring, e.g. pyrrolidino, piperidino, morpholino, piperazino, thiamorpholino, 1,1-dioxothiamorpholino, homomorpholino and hexamethyleneimino. Examples of the optional substituents (R$^3$) which may be present on a second nitrogen atom in the ring are methyl, ethyl, butyl, hexyl, benzyl, and phenethyl. The carbon atoms of the heterocyclic rings may for example be substituted by methyl, ethyl or butyl. Y is preferably a morpholino or piperidino group.

When R$^2$ is a substituted alkyl group, the alkylene portion may for example contain 1-3 carbon atoms (e.g. methylene, ethylene or propylene) and is preferably a methylene group.

In R$^2$ groups of the type (i) (a), the phenyl group may be substituted by, for example, methyl, ethyl, t-butyl, cyclohexyl, benzyl, phenethyl, or phenyl (optionally substituted by methyl, ethyl, methoxy or butoxy) groups.

In R$^2$ groups of the type (i) (b), the thienyl group may be substituted by, for example, methyl, ethyl, methoxy, ethoxy, cyclohexyl or phenyl (optionally substituted by methyl, ethyl, methoxy, ethoxy, chloro or bromo) groups.

R$^2$ is preferably a benzyl group in which the phenyl group is substituted by thienyl or phenyl (which phenyl group itself may be optionally substituted by $C_{1-4}$ alkyl or $C_{1-4}$ alkoxy); or cinnamyl.

Particularly preferred R$^2$ groups are benzyl groups in which the phenyl portion is substituted (preferably in the para-position) by a phenyl, tolyl or methoxyphenyl group.

X is preferably cis —CH=CH—. W may for example contain 1-5 carbon atoms in a straight or branched chain, and is preferably —CH$_2$CH$_2$—.

In general, the compounds of formula (1) in which the carbon atom carrying the —(CH$_2$)$_2$XWCOOH group is in the R-configuration (and mixtures containing this isomer) are preferred, i.e. the 1R-isomers.

Thus, particularly preferred compounds of formula (1) are those in which W is —CH$_2$CH$_2$—, X is cis —CH=CH—, Y is morpholino or piperidino, and R$^2$ is benzyl in which the phenyl group is substituted by phenyl, tolyl or methoxyphenyl, and the physiologically accetable salts and solvates thereof.

Important compounds of this type are [1α(Z), 2β, 3β, 5α]-(±)-7-[5-[[(1,1'-biphenyl)-4-yl]methoxy]-3-hydroxy-2-(4-morpholinyl)cyclopentyl]-4-heptenoic acid and its 1R-isomer; [1α(Z), 2β, 3β, 5α]-(±)-7-[5-[[(1,1'-biphenyl)-4-yl]methoxy]-3-hydroxy-2-(1-piperidinyl)cyclopentyl]-4-heptenoic acid and its 1R-isomer; and the physiologically acceptable salts and solvates (e.g. hydrates) thereof. The 1R-isomers of these compounds are particularly important, especially the 1R-isomer of the hydrochloride salt of the just mentioned piperidinyl compound.

The synthesis of compounds of formula (1) involves a complex multi-stage reaction sequence and British Patent Specification 2097397A describes several possible alternative routes. At some stage, these routes usually include the step of converting an α-hydroxy cyclopentane intermediate into a β-hydroxy cyclopentane intermediate, for example by first oxidising the α-hydroxy compound to form a cyclopentanone and then reducing the latter to form the β-hydroxy compound. It is however also possible to use a sequence where the last step is the epimerisation of the α-hydroxy group of the α- hydroxy cyclopentane corresponding to the desired product.

In view of the number and complexity of the synthetic routes available, many factors have to be taken into account when considering the production of any particular compound of formula (1). It is not only desirable to optimise the synthesis in terms of the yield, physical form and purity of the required product, but also to establish new techniques which can be applied commercially and are thus available for consideration as alternatives to the known methods.

We have now found that compounds of formula (1) can be prepared very satisfactorily by hydrolysing a corresponding ester, amide, nitrile or ortho-ester of formula (2) below. This method has not been suggested before and is advantageous in that the quality and/or yield of the final product can be improved.

We have also found that the compounds of formula (1) are preferably prepared by reducing and subsequently or simultaneously hydrolysing a corresponding cyclopentanone ester, amide, nitrile or ortho-ester of formula (3) as defined below. A particular advantage of this method is that the intermediates and reaction conditions can be chosen so that a separate hydrolysis step is not required and the product is obtained directly in a desirable form.

We have also found that the intermediates of formula (3) are preferably prepared by oxidising the corresponding α-hydroxy cyclopentane ester, amide, nitrile or ortho-ester. In this respect we have thus found that in converting an α-hydroxy cyclopentane intermediate into the required β-hydroxy product, overall advantages can be obtained by performing the necessary oxidation and reduction steps on a starting material in which the side chain —COOH group has been previously modified to form an ester, amide, nitrile or orthoester group.

Thus in one aspect the invention provides a process for the preparation of a compound of formula (1) or a salt or solvate thereof, which comprises hydrolysing a corresponding compound of formula (2)

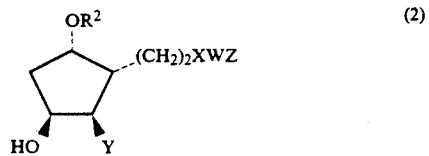

where $R^2$, Y, X and W are as defined above and Z is
(a) —$CO_2R^1$ where $R^1$ is
 (1) —$CR^4R^5R^6$ in which $R^4$ and $R^5$ are each phenyl (optionally substituted by $C_{1-4}$ alkyl, $C_{1-4}$ alkoxy, di-($C_{1-4}$) alkylamino, nitro or halogen) and $R^6$ is a hydrogen atom or a substituted or unsubstituted phenyl group as defined for $R^4$ and $R^5$
 (2) —$SiR^7R^8R^9$ where $R^7$, $R^8$ and $R^9$ are aryl (e.g. phenyl) or $C_{1-6}$ alkyl
 (3) —$CH_2CCl_3$
 (4) —$CH_2CH=CH_2$
 (5) —$CH(R^{10})BCH_2R^{11}$ where B is —O— or —S—, and where $R^{10}$ and $R^{11}$ are —H or $C_{1-4}$ alkyl (e.g. —$CH_2OCH_3$, —$CH(CH_3)OCH_2CH_3$ or —$CH_2SCH_3$) or where $R^{10}$ and $R^{11}$ together represent —$(CH_2)_2$— or —$(CH_2)_3$— (e.g. tetrahydrofuran-2-yl or tetrahydropyran-2-yl)
(b) —$CONR_2^{12}$ where $R^{12}$ is H or $C_{1-4}$ alkyl
(c) —CN, or
(d) —$C(OCH_2)_3CR^{13}$) where $R^{13}$ is $C_{1-4}$ alkyl.

In a further aspect the invention provides a process for the preparation of a compound of formula (1) or a salt or solvate thereof, which comprises reducing and simultaneously or subsequently hydrolysing a corresponding cyclopentanone, of formula (3) as defined below. The reduction and hydrolysis steps may be performed as generally described below with respect to the compound of formula (3) and formula (2).

Z is preferably a group (a) (1), for example where $R^1$ is triphenylmethyl (in which the phenyl groups are optionally substituted by methyl, methoxy or nitro) or diphenylmethyl (in which the phenyl groups are optionally substituted by halogen, methyl methoxy or dimethylamino). More preferably, $R^1$ is triphenylmethyl.

When $R^1$ is a group of type (a) (5), it is preferably tetrahydropranyl.

The hydrolysis of the derivatives of formula (2) in which Z is a group of the type (a), can in general be effected under acidic or basic conditions, for example in an organic or aqueous organic solvent and at any suitable temperature up to and including reflux.

Suitable bases include inorganic bases such as NaOH and KOH. Suitable acids include inorganic acids such as hydrochloric acid and organic acids such as trifluoroacetic acid or acetic acid. Suitable solvents for such hydrolyses include tetrahydrofuran, dioxan, ether, aqueous ether, $CH_2Cl_2$, toluene, $CH_3CN$ and aqueous alcohols.

Esters in which $R^1$ is a group (2) may also be removed using a fluoride (e.g. tetra-n-butylammonium fluoride, KF or HF), for example using tetrahydrofuran or aqueous $CH_3CN$ as the reaction solvent.

Esters in which $R^1$ is $CH_2CCl_3$ may also be removed by reduction e.g. with a metal such as zinc under midly acidic conditions for example using an aqueous phosphate buffer. Tetrahydrofuran, dioxan and dimethoxyethane are suitable solvents.

When $R^1$ is a group of type (5) and B is S, hydrolysis may also be effected in the presence of $Hg^{II}$ salts e.g. mercuric trifluoroacetate or $HgCl_2$, for example using aqueous $CH_3CN$ as solvent. These esters may also be hydrolysed in the presence of $Ag^{II}$ salts (e.g. $AgNO_3$), for example using aqueous tetrahydrofuran, dioxan, dimethoxyethane or $CH_3CN$ as solvent.

The hydrolysis of the derivatives of formula (2) in which Z is a group of the type (b) or (c) can in general be effected using an inorganic base (e.g. KOH) in a suitable solvent such as aqueous ethanol or ethylene glycol at a temperature up to and including reflux.

The hydrolysis of the derivatives of formula (2) in which Z is a group of the type (d) can in general be effected using mild acidic hydrolysis (e.g. using acetic acid or an acidic phosphate buffer) at a temperature of 5° to 35° C., e.g. room temperature.

The acid of formula (1) produced may be isolated in the form of a salt, for example a salt with an inorganic acid, such as hydrochloric acid. This is particularly convenient and advantageous when the hydrolysis is effected with the same acid; salt formation and hydrolysis then take place in the same reaction step.

If desired, the free acid may be liberated from a salt initially formed and converted into another salt if required. One salt may be converted into another, e.g. by exchange of cation.

In general, salt formation may be effected in organic or aqueous organic solvents at temperatures of for example 0° C. to room temperature. Examples of suitable organic solvents are ether, ethyl acetate, CH$_2$Cl$_2$ and dimethoxyethane.

Salts of inorganic bases may be prepared by adding the base to a solution of the acid of formula (1), e.g. in an aqueous organic solvent. Certain salts may also be prepared by exchange of cation; for example, a calcium salt may be prepared by addition of a calcium salt (e.g. the chloride or acetate) to a solution of a salt of a compound of formula (1), e.g. an amine or alkali metal salt.

The process of the invention is thus particularly useful in preparing a salt of a compound of formula (1) by treating a compound of formula (2) (e.g. a compound in which Z is a group (a), particularly a group of the type (a) (1), e.g. where R$^1$ is triphenylmethyl) with an acid or a base. Thus for example a hydrochloride of a compound of formula (1) may be prepared by treating a solution of the compound of formula (2) as just mentioned with hydrogen chloride or hydrochloric acid. This method is particularly suitable in the preparation of the preferred compounds of formula (1) described above.

The compounds of formula (2) may be prepared by reducing the corresponding cyclopentanone of formula (3)

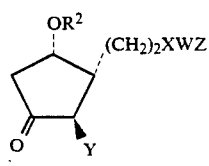

(3)

In some circumstances, particularly when Z is a group of the type (a) (1) (e.g. trityl), hydrolysis of the compound of formula (2) produced occurs either during reduction or during the isolation of the product, with the advantage that no separate hydrolysis step is necessary. Thus, the compounds of formula (1) are preferably prepared by reducing and simultaneously or subsequently hydrolysing the corresponding compound of formula (3).

The reduction may for example be effected with a selective reducing agent such as diisobutylaluminium-2,6-di-t-butyl-4-methylphenoxide, lithium trisiamylborohydride, 2,6-di-tert-butyl-4-methylphenoxymagnesium hydride or potassium tri-isopropoxyborohydride, or tri-isobutylaluminium. The reaction temperature may be from $-10°$ to $-78°$ C. Tetrahydrofuran and toluene are suitable solvents.

The compounds of formula (3) are preferably prepared by oxidising a corresponding α-hydroxy compound of formula (4)

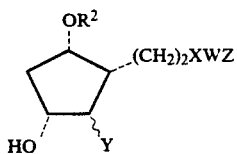

(4)

Suitable methods of oxidation are described in British Patent Specification 2075503A.

The compounds of formula (4) in which Z is a group of the type (a) may be prepared by esterification of the corresponding carboxylic acid, i.e. the compound of formula (4) in which Z represents —COOH. Conventional esterification methods may be used.

Thus, compounds of formula (4) in which Z is a group of the type (a) (1), (2), (4) or (5) may thus be prepared by reacting the corresponding carboxylic acid with an appropriate halide R$^1$Hal where Hal represents halogen. The reaction is carried out in the presence of a suitable base, e.g. potassium t-butoxide or a sterically hindered amine such as N,N-diisopropylethylamine or triethylamine, in a suitable solvent (such as CH$_3$CN, CH$_2$Cl$_2$ or dimethylsulphoxide), for example at a temperature from 0° C. to room temperature.

Esters in which R$^1$ is —CH$_2$CCl$_3$ may be prepared by treating a reactive derivative of the corresponding carboxylic acid with CCl$_3$CH$_2$OH. The reaction may for example be carried out at room temperature using a solvent such as acetone and, where appropriate, in the presence of pyridine.

The reactive derivative is conveniently a mixed anhydride of the acid, formed for example by treatment of the acid with a chloroformate in the presence of a suitable base, e.g. triethylamine or pyridine at $-10°$ C.

The chloroformate may for example be a C$_{1-6}$ alkyl (e.g. iso-butyl), aryl (e.g. phenyl) or aralkyl (e.g. benzyl) chloroformate.

The parent carboxylic acids required as starting materials in the esterification reactions may be prepared by the methods described in British Patent Specification 2075503A.

Compounds of formula (4) in which Z is a group of the type (b) may be prepared by amidation of the parent carboxylic acid i.e. the corresponding compound in which Z is —COOH. Conventional methods for converting acids into amides may be used.

For example, a reactive derivative of the carboxylic acid may be treated with ammonia or an amine (R$^{12}$)$_2$NH in a suitable solvent, e.g. acetone or acetonitrile. The reactive derivative may for example be as described above.

Compounds of formula (4) in which Z is a group of the type (c) or (d) in which X is cis —CH=CH— may be prepared by reacting an aldehyde of formula (5)

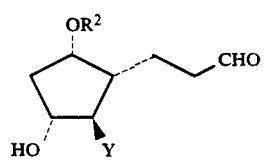

(5)

with an appropriate Wittig reagent, e.g. a phosphorane of formula (R$^{14}$)$_3$P=CHWZ (where R$^{14}$ is C$_{1-6}$ alkyl or aryl, e.g. monocyclic aryl such as phenyl). Suitable reaction solvents include hydrocarbons (e.g. benzene and toluene), ethers (e.g. tetrahydrofuran), dialkylsulphoxides (e.g. dimethylsulphoxide), alcohols and halogenated hydrocarbons. The reaction may be carried out at any suitable temperature from $-70°$ to 50° C., preferably at room temperature. The group X in the product may subsequently be modified as desired.

The preparation of the intermediates of formula (5) is described in British Patent Specification 2075503A.

When a specific enantiomer of formula (1) is required, starting materials having the desired sterochemical configuration should be used in the above processes. Such starting materials may for example be prepared from an enantiomeric bicycloheptenone as described in European Patent Specification 74856, using the methods generally described in UK Patent Specifications 2028805A, 2075503A and 2097397A.

The following examples illustrate the invention. Temperatures are in °C. The following abbreviations are used:

| | |
|---|---|
| T.l.c. | Thin layer chromatography using SiO$_2$; |
| PE | petroleum ether (b.p. 40–60°); |
| THF | tetrahydrofuran |
| DMSO | dimethyl sulphoxide |
| Dibal | diisobutylaluminium hydride |
| ER | ether |
| DMF | dimethylformamide |
| EA | ethyl acetate |

Chromatography was carried out using silica gel unless otherwise stated. 'Dried' refers to drying with MgSO$_4$. 'Hyflo' is a filtration aid.

The preparation of Intermediate 1 is described in British Patent Specification 2075503A.

INTERMEDIATE 1

[1R-[1α(Z),2β,3α,5α]]-(+)-7-[5-[[(1,1'-Biphenyl)-4-yl]methoxy]-3-hydroxy-2-(4-morpholinyl)cyclopentyl]-4-heptenoic acid The preparations of Intermediates 2–6 are described in British Patent Specification 2097397A.

INTERMEDIATE 2

[1R-(endo, anti)]-(+)-5-Hydroxy-7-(1-piperidinyl)-bicyclo[2.2.1]heptan-2-one

INTERMEDIATE 3

[1R-(1α,2β,3α,5α)]-(+)-5-[[(1,1'-Biphenyl)-4-yl]methoxy]-3-hydroxy-2-(1-piperidinyl)cyclopentane acetaldehyde

INTERMEDIATE 4

[1R-[1α(Z),2β,3β,5α]]-(+)-7-[5-[[(1,1'-Biphenyl)-4-yl]methoxy]-3-hydroxy-2-(1-piperidinyl)cyclopentyl]-4-heptenoic acid

INTERMEDIATE 5

[1R-[1α(Z),2β,3β,5α]]-(+)-7-[5-[[(1,1'-Biphenyl)-4-yl]methoxy]-3-hydroxy-2-(4-morpholinyl)cyclopentyl]-4-heptenoic acid

INTERMEDIATE 6

[1R-(1α,2β,3β,5α)]-(+)-5-[[(1,1'-Biphenyl)-4-yl]methoxy]-3-hydroxy-2-(1-piperidinyl)cyclopentanpropanal The preparations of Intermediates 7 and 8 are described in British Patent Specification 2108116A

INTERMEDIATE 7

[1R-[1α(Z),2β,3β,5α]]-(+)-2-Propenyl 7-[5-[[(1,1'-Biphenyl)-4-yl]methoxy]-3-hydroxy-2-(1-piperidinyl)-cyclopentyl]-4-heptenoate

INTERMEDIATE 8

[1R-[1α(Z),2β,3β,5α]]-(+)-(Methylthio)methyl 7-[5-[[(1,1'-Biphenyl)-4-yl]methoxy]-3-hydroxy-2-(1-piperidinyl)cyclopentyl]-4-heptenoate

INTERMEDIATE 9

[1R-(1α,2β,3α,5α)]-(+)-5-[[(1,1'-Biphenyl)-4-yl]methoxy]-3-hydroxy-2-(1-piperidinyl)cyclopentanepropanal A solution of Intermediate 3 (13 g) in toluene (39 ml) was added dropwise to a suspension of potassium tert-butoxide (5.96 g) in toluene (52 ml). Methoxymethyltriphenylphosphonium chloride (15.93 g) was added and the mixture stirred overnight (18 h).

2N Hydrochloric acid (52 ml) was added and the mixture heated with stirring at 40° for 30 min. Solid K$_2$CO$_3$ (13 g) was added, the organic phase separated, washed with water (52 ml) and dried azeotropically to give a solution of Intermediate 9 in toluene (115 ml). A portion of the solution (8.8 ml), was purified by chromatography eluting with 9:1 EA-methanol to give the title compound as a foam (0.53 g).

T.l.c. 4:1 EA-methanol Rf 0.15.

$[\alpha]_D^{23} = +42.8°$ (CHCl$_3$).

INTERMEDIATE 10

[1R-[1α(Z),2β,3α,5α]]-(+)-7-[5-[[(1,1'-Biphenyl)-4-yl]methoxy]-3-hydroxy-2-(1-piperidinyl)cyclopentyl]-4-heptenoic acid, hydrochloride To a solution of potassium tert-butoxide (21.49 g) in toluene (198 ml) and THF (52 ml) under N$_2$ was added 3-(carboxypropyl)triphenylphosphonium bromide (41.14 g). After 1.5 h a solution of Intermediate 9 (24.5 g) in toluene (220 ml) was added and the mixture stirred for 3 h. Water (125 ml) was added, the mixture vigorously shaken and the phases separated. The aqueous phase was washed with toluene (2×225 ml) (discarded), then acidified (to pH 7.5) with 2N hydrochloric acid and extracted with CH$_2$Cl$_2$ (2×225 ml). The combined CH$_2$Cl$_2$ extracts were dried and evaporated to give the title compound, base (24.47 g) as a gum.

A solution of the base (93 mg) in CH$_2$Cl$_2$ (1.5 ml) was treated with an excess of ethereal hydrogen chloride. The solvents were removed and the residual oil triturated with ER (5 ml). The resulting solid was filtered, washed with ER and dried to give the title compound (92 mg)

m.p. 132.5°–136° (softens at 128°).

$[\alpha]_D^{25} = +52.9°$ (CHCl$_3$).

INTERMEDIATE 11

[1R-(endo, anti)]-(+)-5-[[4'-Methoxy(1,1'-biphenyl)-4-yl]methoxy]-7-(1-piperidinyl)bicyclo[2.2.1]heptan-2-one A mixture of Intermediate 2 (30.51 g), benzyltriethylammonium chloride (6.65 g) and 4-(bromomethyl)-4'-methoxy(1,1'-biphenyl)(52.6 g) in CH$_2$Cl$_2$ (365 ml) and 17N NaOH (325 ml) was vigorously stirred at ambient temperature for 18 h. The mixture was diluted with water (1 l) and extracted with CH$_2$Cl$_2$ (3×150 ml). The combined extracts were dried and evaporated and the residue was purified by chromatography using ER-PE (1:1 followed by 7:3) as eluent to give the title compound (40.2 g).

A portion was recrystallised from EA-PE m.p. 109.5°–110.5°.

$[\alpha]_D^{23.7} = +22.7°$ (CHCl$_3$)

INTERMEDIATE 12

[1R-(endo,anti)]-(−)-6-[[4'-Methoxy(1,1'-biphenyl)-4-yl]methoxy]-8-(1-piperidinyl)-2-oxabicyclo[3.2.1]octan-3-one A solution of peracetic acid in acetic acid (5.6M, 124 ml) was added slowly to a stirred mixture of Intermediate 11 (42 g) in $CH_2Cl_2$ (235 ml), 2N $H_2SO_4$ (29 ml) and water (159 ml) and the mixture stirred at ambient temperature for 24 h. The mixture was adjusted to ca. pH7 using 5N NaOH and pH 6.5 phosphate buffer then extracted with $CH_2Cl_2$ (3×200 ml). The combined organic extracts were added to an excess of sodium metabisulphite solution and stirred for 24 h. The mixture was extracted with EA (1×500, 2×250 ml) and the combined organic extracts were dried and evaporated and the residue was purified by chromatography using 1:1 EA-PE as eluent to give the title compound (24.4 g).

A portion was recrystallised from EA-PE m.p. 116.5°–117.5°.

$[\alpha]_D^{23.4} = -24.5°$ ($CHCl_3$)

INTERMEDIATE 13

[1R-(1α,2β,3α,5α)]-( )-3-Hydroxy-5-[[4'-methoxy(1,1'-biphenyl)-4-yl]methoxy]-2-(1-piperidinyl)cyclopentane acetaldehyde DIBAL in hexane (1M, 114 ml) was added slowly to a cold (−70°) stirred solution of Intermediate 12 (24 g) in $CH_2Cl_2$ (240 ml). After 0.5 h methanol (240 ml) was added, slowly at first, and the mixture was stirred at ambient temperature for 16 h. The precipitate was filtered off and the filtrate evaporated to give the title compound as a foam (24.1 g).

T.l.c. 9:1 EA-methanol Rf 0.35.

INTERMEDIATE 14

[1R-(1α,2β,3α,5α)]-(+)-4-[[4'-Methoxy(1,1'biphenyl)-4-yl]methoxy]-3-(3-methoxy-2-propenyl)-2-(1-piperidinyl)cyclopentanol, hydrochloride A solution of Intermediate 13 (24.1 g) in THF (75 ml) was added to a cooled (−5° to 0°), stirred solution of the ylid derived from methoxymethyltriphenylphosphonium chloride (78 g) and potassium tert-butoxide (25.5 g) in THF (800 ml). After 1.5 h methanol (100 ml) was added and the solvents removed in vacuo. The residue in pH6.5 phosphate buffer (600 ml) was extracted with $CH_2Cl_2$ (3×150 ml) and the combined extracts were dried and evaporated. The residue was purified by chromatography using 4:1 EA-methanol as eluent to give the title compound, base as an oil (24.8 g).

A portion was converted into the hydrochloride salt m.p. 150°–151°(dec).

$[\alpha]_D^{23.1} = +38.1°$ ($CHCl_3$)

INTERMEDIATE 15

[1R-(1α,2β,3α,5α)]-(+)-3-Hydroxy-5-[[4'-methoxy(1,1'-biphenyl)-4-yl]methoxy]-2-(1-piperidinyl)cyclopentanepropanel, hydrochloride A solution of Intermediate 14 (24.3 g) in 2N HCl (55 ml) and acetone (250 ml) was stirred at ambient temperature for 1 h. Most of the acetone was removed in vacuo and the residue in water was extracted with $CH_2Cl_2$ (3×150 ml). The combined extracts were dried and evaporated to give a solid (23.6 g). A portion was triturated with ether to give the title compound as a powder m.p. 182°–185° (dec).

$[\alpha]_D^{22.7} = +51.5°$ ($CHCl_3$)

INTERMEDIATE 16

[1R-[1α(Z),2β,3α,5α]]-(+)-Methyl 7-[3-Hydroxy-5-[[4'-methoxy(1,1'-biphenyl)-4-yl]methoxy]-2-(1-piperidinyl)cyclopentyl]-4-heptenoate, hydrochloride.

A suspension of Intermediate 15 (23.6 g) in THF (300 ml) was added to the ylid derived from 3-(carboxypropyl)triphenylphosphonium bromide (69.5 g) and potassium tert-butoxide (36.3 g) in THF (1000 ml). After 2 h water (200 ml) was added and the THF was removed in vacuo. The residue was diluted with water (250 ml) and extracted with ER (3×200 ml; discarded). The aqueous layer was neutralised using 5N HCl and extracted with $CH_2Cl_2$ (3×200 ml). The combined extracts were dried and evaported and the residue was left to stand in methanol (250 ml) containing concentrated sulphuric acid (5 ml) for 19 h. Most of the methanol was removed in vacuo and the residue neutralised using 2N NaOH and pH 6.5 phosphate buffer (150 ml). The mixture was extracted with EA (3×150 ml) and the combined extracts were dried and evaporated. The residue was purified by chromatography using initially 9:1 ER-methanol followed by 4:1 ER-methanol as eluent to give the title compound, base as an oil (15.9 g). A portion was converted into the hydrochloride salt m.p. 122°–125° (dec).

$[\alpha]_D^{22.5} = +55.9°$ ($CHCl_3$)

INTERMEDIATE 17

[1R-[1α(Z),2β,3α,5α]]-(+)-7-[3-Hydroxy-5-[4'-methoxy(1,1'-biphenyl)-4-yl]methoxy]-2-(1-piperidinyl)cyclopentyl]-4-heptenoic acid, hydrochloride A mixture of Intermediate 16 (6.59 g), 5N NaOH (7.6 ml) and methanol (65 ml) was vigorously stirred at ambient temperature for 24 h. Most of the methanol was removed in vacuo and the residue in pH 6.5 phosphate buffer (170 ml) was extracted with $CH_2Cl_2$ (3×50 ml). The combined extracts were dried and evaporated to give a foam (6.4 g). A portion of the base in ER-$CH_2Cl_2$ was treated with an excess of ethereal hydrogen chloride to give the title compound m.p. 137°–138.5°.

$[\alpha]_D^{24.1} = +51°$ ($CHCl_3$)

INTERMEDIATE 18

[1R-[1α(Z),2β,3α,5α]]-(+)-Triphenylmethyl 7-[5-[[(1,1'-Biphenyl)-4-yl] methoxy]-3-hydroxy-2-(1-piperidinyl)cyclopentyl]-4-heptenoate Triethylamine (2.49 ml) was added to a cold (5°) solution of Intermediate 10, base (5.88 g) and trityl chloride (4.4 g) in $CH_2Cl_2$ (24 ml). The mixture was stirred for 30 min then water (60 ml) and further $CH_2Cl_2$ (30 ml) added. The organic phase was separated then evaporated in vacuo. The residue was azeotroped with $CH_2Cl_2$ (60 ml) to give an oil (10.13 g) which was chromatographed on alumina (500 g), eluting with EA to give the title compound as an oil (5.14 g). T.l.c. (Al$_2O_3$) 49:1 EA-methanol Rf 0.52.

$[\alpha]_D^{25} = +34.2°$ ($CHCl_3$)

INTERMEDATE 19 a) [1R-[1α(Z),2β,5α]]-(−)-Triphenylmethyl 7-[5[[(1,1'-Biphenyl)-4-yl]methoxy]-3-oxo-2-(1-piperidinyl)cyclopentyl]-4-heptenoate Triethylamine (9.17 ml) was added at 2° to a stirred solution of Intermediate 18 (6.47 g) in $CH_2Cl_2$ (65 ml), followed by a solution of pyridine/$SO_3$ complex (5.75 g) in DMSO (65 ml). The resulting solution was stirred at 3°-5° for 2 h and quenched by the dropwise addition of ice-water (65 ml). The reaction mixture was extracted with ER (2×65 ml) and the extract washed with water (65 ml), 1M citric acid (4×10 ml) and water (10 ml). Evaporation of the dried ($Na_2SO_4$) solvents gave the title compound as a foam (5.9 g).

I.r. ($CHBr_3$) 1740 cm$^{-1}$.

$[α]_D^{24} = -12°$ ($CHCl_3$). The following compounds were prepared in a similar manner:

b) [1R-[1α(Z), 2β,5α]]-(−)-Diphenylmethyl 7-[5-[[(1,1'-Biphenyl)-4-yl] methoxy]-3-oxo-2-(1-piperidinyl)cyclopentyl]-4-heptenoate, from Intermediate 22. Purification by chromatography using 3:2 ER-PE as eluent.

Analysis Found: C,80.5; H,7.5; N,2.2; $C_{43}H_{47}NO_4$ requires C,80.5; H.7.4; N,2.2%.

$[α]_D^{20.3} = -13°$ ($CHCl_3$).

c) [1R-[1α(Z),2β,5α]]-(—)-(Methoxymethyl) 7-[5-[[(1,1'-Biphenyl)-4-yl]methoxy]-3-oxo-2-(1-piperidinyl)-cyclopentyl]-4-heptenoate, from Intermediate 20d. Purification by chromatography using 1:1 ER-PE as eluent.

Analysis Found: C,73.6; H,8.3; N,2.6; $C_{32}H_{41}NO_5$ requires C,73.9; H,8.0; N,2.7%.

$[α]_D^{21} = -14.4°$ ($CHCl_3$).

d) [1R-[1α(Z),2β,5α]]-( )-Triphenylmethyl 7-[5-[[4'-Methoxy(1,1'-biphenyl)-4-yl]methoxy]-3-oxo-2-(1-piperidinyl)cyclopentyl]-4-heptenoate, from Intermediate 17. Purification by chromatography using 1:1 ER-PE (b.p. 60°-80°) as eluent.

T.l.c. 1:1 ER-PE (b.p. 60°-80°) Rf 0.29.

e) [1R-[1α(Z),2β,5α]]-(—)-7-[5-[[(1,1'-Biphenyl)-4-yl]methoxy]-2-(4-morpholinyl)-3-oxocyclopentyl]-4-heptenamide, compound with ethyl acetate (4:1), from Intermediate 23e. Purification by chromatography using 9:1 EA-methanol as eluent.

Analysis Found: C,72.0; H,7.6; N,5.55; $C_{29}H_{36}N_2O_4 \cdot 0.25 C_4H_8O_2$ requires C,72.1; H,7.7; N,5.6%.

$[α]_D^{24} = -11.4°$ ($CHCl_3$).

INTERMEDIATE 20 a) [1R-[1α(Z),2β,3β,5α]]-( )-Triphenylmethyl 7-[5-[[(1,1'-Biphenyl)-4-yl]methoxy]-3-hydroxy-2-(1-piperidinyl)cyclopentyl]-4-heptenoate Trityl chloride (0.56 g) was added to a stirred, ice cooled, solution of the Intermediate 4 (0.376 g) in $CH_2Cl_2$ (5 ml) containing triethylamine (0.45 ml). After 1.25 h the mixture was diluted with pH 6.5 phosphate buffer (50 ml) and the product extracted into EA (2×50 ml). The EA extract was dried and evaporated in vacuo and the residue was purified by chromatograhy using 100:1 ER-triethylamine as eluent to give the title compound (0.28 g) as a gum.

T.l.c. ($Al_2O_3$) $Et_2O$ Rf 0.7.

The following compounds were prepared in a similar manner:

b) [1R[1α(Z),2β,3β,5α]]-(+)-(Tetrahydro[2H]pyran-2-yl) 7-[5-[[(1,1'-Biphenyl)-4-yl]methoxy]-3-hydroxy-2-(1-piperidinyl)cyclopentyl]-4-heptenoate, from Intermediate 4 and 3,4-dihydro[2H]pyran in THF. Purification by chromatography on alumina using ER followed by EA and 19:1 EA-methanol as eluents.

Analysis Found: C,74.3; H,8.7; N,2.6; $C_{35}H_{47}NO_5$ requires C,74.8; H,8.4; N,2.5%.

$[α]_D^{20} = +59°$ ($CHCl_3$).

c) [1R-[1α(Z),2β,3β,5α]]-(+)-(1-Ethoxyethyl) 7-[5-[[(1,1'-Biphenyl)-4-yl]methoxy]-3-hydroxy-2-(1-piperidinyl)cyclopentyl]-4-heptenoate, from Intermediate 4 and 1-chloroethyl ethyl ether in THF. Purification by chromatography on alumina using 1:1 ER-PE as eluent.

Analysis Found: C,74.6; H,8.6; N,2.9; $C_{34}H_{47}NO_5$ requires C,74.3; H.8.6; N,2.55%.

$[α]_D^{19} = +61.8°$ ($CHCl_3$).

d) [1R-[1α(Z),2β,3α,5α]]-(+)-(Methoxymethyl) 7-[5-[[(1,1'-Biphenyl)-4-yl]methoxy]-3-hydroxy-2-(1-piperidinyl)cyclopentyl]-4-heptenoate, from Intermediate 10, base chloromethyl methyl ether and diisopropylethylamine in DMF. Purification by chromatography using 99:1 EA-$Et_3N$ as eluent.

T.l.c. 89:10:1 EA-methanol-$Et_3N$ Rf 0.4.

$[α]_D^{23} = +62.7°$ ($CHCl_3$).

e) [1R-[1α(Z),2β,3β,5α]]-( )-(1,1-Dimethylethyl)-dimethylsilyl 7-[5-[[(1,1'-Biphenyl)-4-yl]methoxy]-3-hydroxy-2-(4-morpholinyl) cyclopentyl]-4-heptenoate, from Intermediate 5 and tert-butyldimethyl-silyl chloride.

T.l.c. ER Rf 0.31.

INTERMEDIATE 21 a) [1R-[1α(Z),2β,5α]]-( )-(1,1-Dimethylethyl)dimethylsilyl 7-[5-[[(1,1'-Biphenyl)-4-yl]methoxy]-3-oxo-2-(1-piperidinyl)cyclopentyl]-4-heptenoate $Et_3N$ (0.8 ml) followed by tert-butyldimethylsilyl chloride (0.42 g) were added to a cooled (0°), stirred suspension of Intermediate 10, camphor sulphonate (1.6 g) in $CH_2Cl_2$ (7 ml). After 0.5 h more $Et_3N$ (4 ml) followed by a solution of pyridine-sulphur trioxide complex (2 g) in DMSO (7 ml) were added and stirring was continued for 4 h. The mixture was diluted with pH 6 phosphate buffer (100 ml) and extracted with ER (2×100 ml). The combined extracts were dried and evaporated and the residue was purified by chromatography using 1:1 ER-PE as eluent to give the title compound as an oil (0.8 g).

I.r. ($CHBr_3$) 1735, 1705 cm$^{-1}$.

The following compound was prepared in a similar manner b) [1R-[1α(Z),2β,5α]]-( )-(1,1-Dimethylethyl)diphenylsilyl 7-[5-[[(1,1'-Biphenyl)-4-yl]methoxy]-3-oxo-2-(1-piperidinyl)cyclopentyl]-4-heptenoate, from Intermediate 10, camphor sulphonate using tert-butyl-diphenylsilyl chloride.

I.r. ($CHBr_3$) 1730 cm$^{-1}$.

INTERMEDIATE 22

[1R-[1α(Z),2β,3α,5α]]-(+)-Diphenylmethyl 7-[5-[[(1,1'-Biphenyl)-4-yl]methoxy]-3-hydroxy-2-(1-piperidinyl)cyclopentyl]-4-heptenoate Diphenyldiazomethane (1.1 g) was added to a solution of Intermediate 10, base (1 g) in $CH_2Cl_2$ (30 ml). After 18 h at ambient temperature the solvent was evaporated and the residue was purified by chromatography on alumina using 19:1 ER-methanol as eluent to give the title compound as an oil (1.22 g).

Analysis Found: C,80.3; H,7.5; N,2.6. $C_{43}H_{49}NO_4$ requires C,80.2; H,7.7; N,2.2%.

$[\alpha]_D^{20.3} = +52°$ (CHCl$_3$).

INTERMEDIATE 23 a) [1R-[1α(Z),2β,3β,5α]]-(+)-N,N-Dimethyl 7-[5-[[(1,1'-Biphenyl)-4-yl]methoxy]-3-hydroxy-2-(1-piperidinyl)cyclopentyl]-4-heptenamide Isobutylchloroformate (0.51 ml) was added to a cold (0°) stirred mixture of Intermediate 4, hydrochloride (1 g) and Et$_3$N (1.08 ml) in acetone (75 ml). After 0.5 h dimethylamine (4 ml) was added and the mixture left for 2 h. The mixture was diluted with pH 6.5 phosphate buffer (75 ml) and most of the acetone was removed in vacuo. The residue was extracted with EA and the combined extracts were dried and evaporated. The residue was purified by chromatography using 80:20:1 EA-methanol-ammonia as eluent to give the title compound as an oil (0.815 g).

I.r. (CHBr$_3$) 3590, 1635 cm$^{-1}$.

$[\alpha]_D^{23} = +63.2°$ (CHCl$_3$).

The following compounds were prepared in a similar manner:

b) [1R-[1α(Z),2β,3β,5α]]-(+)-2,2,2-Trichloroethyl 7-[5-[[(1,1'-Biphenyl)-4-yl]methoxy]-3-hydroxy-2-(1-piperidinyl)cyclopentyl]-4-heptenoate, from Intermediate 4, hydrochloride using 2,2,2-trichloroethanol. Purification by chromatography using 95:5:1 EA-methanol-Et$_3$N as eluent.

Analysis Found: C,63.5; H,6.65; N,2.55. $C_{32}H_{40}Cl_3NO_4$ requires C,63.1; H,6.6; N,2.3%.

$[\alpha]_D^{23} = +59°$ (CHCl$_3$).

c) [1R-[1α(Z),2β,3α,5α]]-(+)-7-[5-[[(1,1'-Biphenyl)-4-yl]methoxy]-3-hydroxy-2-(4-morpholinyl)cyclopentyl]-4-heptenamide, m.p. 111° from Intermediate 1, methane sulphonate and ammonia. Purification initially by chromatography using 7:3 ER-methanol as eluent and then by crystallisation from EA-PE (b.p. 60°-80°).

$[\alpha]_D^{22.1} = +64.2°$ (CHCl$_3$).

Intermediate 24

[1R-[1α(Z),2β,3β,5α]]-(+)-7-[5-[[(1,1'-Biphenyl)-4-yl]methoxy]-3-hydroxy-2-(1-piperidinyl)cyclopentyl]-4-heptenitrile A solution of Intermediate 6 (1 g) in THF (10 ml) was added to the ylid derived from 3-cyanopropyltriphenylphosphonium bromide (2.5 g) and potassium tert-butoxide (0.69 g) in THF (25 ml). After 1 h water (100 ml) was added and the mixture extracted with EA (3×50 ml). The combined extracts were dried and evaporated and the residue was purified by chromatography on alumina using ER as eluent to give the title compound as an oil (0.78 g).

Analysis Found: C,78.3; H,8.5; N,6.5. $C_{30}H_{38}N_2O_2$ requires C,78.6; H,8.4; N,6.1%.

$[\alpha]_D^{23.2} = +69.3°$ (CHCl$_3$).

Intermediate 25

[1R-[1α(Z),2β,3β,5α]]-(+)-7-[5-[[(1,1'-Biphenyl)-4-yl]methoxy]-3-hydroxy-2-(4-morpholinyl)cyclpentyl]-4-heptenamide A solution of Dibal in hexane (1M, 4.2 ml) was added over 5 min to a cooled (0°), stirred solution of 2,6-di-tert-butyl-4-methyl phenol (1.85 g) in dry toluene (20 ml) under nitrogen. After 1 h the solution was cooled to −70° and a solution of Intermediate 19e (0.2 g) in toluene (5 ml) was added, the mixture was stirred at −70° for 1 h then kept at −20° for 18 h. 2N hydrochloric acid (20 ml) was added and the mixture allowed to warm to ambient temperature over 1 h. 2N Na$_2$CO$_3$ solution (20 ml) was added and the mixture was extracted with EA (3×40 ml). The combined extracts were dried and evaporated and the residue was purified by chromatography using 7:3 ER-methanol as eluent to give the title compound as a solid (0.15 g), m.p. 93°-94.5°.

$[\alpha]_D^{22.5} = +61.6°$ (CHCl$_3$).

EXAMPLE 1

[1R-[1α(Z),2β,3β,5α]]-(+)-7-[5-[[(1,1'-Biphenyl)-4-yl]methoxy]-3-hydroxy-2-(1-piperidinyl)cyclopentyl]-4-heptenoic acid, hydrochloride

Method a)

Dibal (1M in hexane, 5.5 ml) was added dropwise at 0°-2° to a stirred solution of 2,6-di-t-butyl-4-methylphenol (2.9 g) in CH$_2$Cl$_2$ (13 ml). The solution was stirred at −5° to 0° for 1 h and then cooled to −20°. A solution of Intermediate 19a (1.3 g) in CH$_2$Cl$_2$ (13 ml) was added at −18° to −20°. The mixture was stirred at this temperature for 2.5 h, 1N hydrochloric acid (20 ml) was then added dropwise, and the mixture was stirred at room temperature for 0.5 h. The phases were separated and the aqueous layer was extracted with CH$_2$Cl$_2$ (10 ml). The organic extracts were combined, washed with brine, dried (Na$_2$SO$_4$) and evaporated to give a yellow gum. The product was triturated with ER to give a pale yellow powder (0.68 g). Recrystallisation from EA-methanol gave the title compound m.p. 128°-130°.

$[\alpha]_D^{23} = +66.5°$ (CHCl$_3$).

T.l.c. 25:15:8:2 EA-iPrOH-H$_2$O-NH$_3$ Rf 0.4.

Method b)

A solution of Intermediate 20a (0.27 g) in acetone (7 ml) and 2N hydrochloric acid (4 ml) was stirred at 20° for 2 h. Most of the acetone was removed in vacuo and the residue extracted with ER (2×15 ml); discarded). The aqueous phase was extracted with CH$_2$Cl$_2$ (2×15 ml), dried, evaporated and the residue triturated with ER to give a solid. Recrystallisation from EA-methanol gave the title compound (104 mg) m.p. 125°-126°.

T.l.c. Identical mixed spot with the product of Method a.

Method c)

A solution of Intermediate 20b (0.142 g) in THF (4 ml) and 2N hydrochloric acid (4 ml) was kept at 20° for 3 h. Most of the THF was removed in vacuo and the residue was diluted with water (2 ml) and extracted with ER (4 ml, discarded). The aqueous layer was extracted with CH$_2$Cl$_2$ (3×6 ml) and the combined extracts were dried and evaporated. The residue was triturated with ER and the resulting solid recrystallised from EA-methanol to give the title compound (0.048 g) m.p. 125°-127°.

T.l.c. Identical mixed spot with the product of Method a.

Method d)

A solution of Intermediate 20c (0.196 g) in THF (3 ml) and 2N hydrochloric acid (2 ml) was kept at 20° for 0.5 h. Most of the THF was removed in vacuo and the residue was diuted with water (6 ml) and extracted with 1:1 PE-ER (7 ml, discarded). The aqueous layer was extracted with $CH_2Cl_2$ (4×7 ml) and the combined extracts were dried and evaporated. The residue was triturated with ER to give the title compound (0.163 g), m.p. 128.5°–129°.

T.l.c. Identical mixed spot with the product of Method a.

Method e)

Intermediate 21a was converted into the title comound following the procedure described for Method a using toluene as solvent, m.p. 124°–128°.

T.l.c. Identical mixed spot with the product of Method a.

Method f)

Dibal (1M in hexane 10 ml) was added dropwise at 0° to a stirred solution of 2,6-di-t-butyl-4-methylphenol (4.4 g) in toluene (15 ml). The solution was stirred at 0° for 1 h then cooled to −60°. A solution of Intermediate 21b (0.7 g) in toluene (5 ml) was added and stirring continued for 0.5 h at −60° and 2 h at −10°. 2N hydrochloric acid (2 ml) was added followed by (after 5 min) pH 6 phosphate buffer (80 ml). The mixture was extracted with $CH_2Cl_2$ (3×50 ml) and the combined extracts were dried and evaporated. The phenolic impurities were removed by chromatography using 9:1 EA-methanol as eluent and the residue in acetone (3 ml) and 5N hydrochloric acid (2 ml) was kept at ambient temperature for 24 h. The acetone was removed in vacuo and the residue was washed with $CH_2Cl_2$ (3×10 ml) and the combined extracts were dried and evaporated. The residue was triturated with ER to give the title compound (0.074 g), m.p. 123°–126°.

T.l.c. Identical mixed spot with the product of Method a.

Method g)

Intermediate 19b was converted into the title compound following the procedure described for Method f, m.p. 124.5–127.5.

T.l.c. Identical mixed spot with the product of Method a.

Method h)

Intermediate 19c was converted into the title compound following the procedure described for Method a using toluene as solvent, m.p. 122°–124°.

T.l.c. Identical mixed spot with the product of Method a.

Method i)

Mercuric trifluoroacetate (0.28 g) in water (0.75 ml) was added to a stirred solution of Intermediate 8 (0.1 g) in $CH_3CN$ (3 ml). After 3 h hydrogen sulphide was passed through the solution until no further precipitate was formed. The solids were removed by filtration ('Hyflo') and the filtrate was evaporated in vacuo. 0.5N Hydrochloric acid (30 ml) was added to the residue and the solution was extracted with $CH_2Cl_2$ (3×15 ml). The combined extracts were dried and evaporated and the residue was triturated with ER to give a solid which was recrystallised from EA-methanol to give the title compound (0.037 g) m.p. 123°–126°.

T.l.c. Identical mixed spot with the product of Method a.

Method j

A solution of Intermediate 7 (75 mg) in 2N NaOH (1 ml) and ethanol (2 ml) was stirred at 20° for 4 h. The mixture was adjusted to pH 1 using 5N hydrochloric acid and was extracted with $CH_2Cl_2$. The combined extracts were washed with water, dried and evaporated and the residue was triturated with ER to give a solid (51 mg). A portion was recrystallised from EA-methanol to give the title compound m.p. 124°–126°.

T.l.c. Identical mixed spot with the product of Method a.

Method k

Intermediate 23a was converted into the title compound following the procedure described for Method j at reflux, m.p. 124°–127°.

T.l.c. Identical mixed spot with the product of Method a.

Method l

A solution of Intermediate 24 (0.1 g) in 5N NaOH (5 ml) and ethanol (10 ml) was heated under reflux for 3.5 h. The solution was adjusted to pH 6 using 2N hydrochloric acid, diluted with pH 6 phosphate buffer (50 ml) and extracted with $CH_2Cl_2$ (3×50 ml). The combined extracts were dried and evaporated and the residue in $CH_2Cl_2$ was treated with an excess of ethereal hydrogen chloride. The solvents were removed and the residue was triturated with ER to give the title compound (0.08 g) m.p. 116°–119°.

T.l.c. Identical mixed spot with the product of Method a.

Method m

A mixture of Intermediate 23b (0.275 g), zinc dust (2 g), $KH_2PO_4$ solution (4 ml) and THF (20 ml) was vigorously stirred for 24 h at ambient temperature. The mixture was filtered and the filtrate was adjusted to pH 1 using 2N hydrochloric acid. Most of the THF was removed in vacuo and the residue was extracted with $CH_2Cl_2$ (2×30 ml). The combined extracts were dried and evaporated to give the title compound as an oil.

T.l.c. Identical mixed spot with the product of Method a.

EXAMPLE 2

[1R-[1α(Z),2β,3β,5α]]-(+)-7-[3-Hydroxy-5-[4'-methoxy(1,1'-biphenyl)-4-yl]methoxy]-2-(1-piperidinyl)cyclopentyl]-4-heptenoic acid, hydrochloride Dibal (1M in hexane, 11 ml) was added dropwise at −5° to a stirred solution of 2,6-di-t-butyl-4-methylphenol (4.84 g) in toluene (15 ml). of Intermediate 19d (0.83 g) in toluene (4 ml) was added and the mixture stirred at −65° for 1h and −10° for 1 h. The mixture was extracted with 2N hydrochloric acid (5×15 ml) and the acidic extracts, along with the precipitated oil were neutralised with 5N NaOH (30 ml) and pH 6.5 phosphate buffer (30 ml). The filtered aqueous solution was extracted with dichloromethane (4×25 ml) and the combined extracts were dried and evaporated. The residue in ER-$CH_2Cl_2$ was treated with an excess of ethereal hydrogen chloride and the resulting solid was recrystallised from $CH_2Cl_2$-iPrOAc to give the title compound (0.191 g) m.p. 124.5°–125.5°.

I.r. ($CHBr_3$) 3300 (br), 2800–2300, 1720 cm$^{-1}$.

$[\alpha]_D^{21.632}$ +65.4° ($CHCl_3$).

EXAMPLE 3

[1R-[1α(Z),2β,3β,5α]]-(+)-7-[5-[[(1,1'-Biphenyl)-4-yl]methoxy]-3-hydroxy-2-(4-morpholinyl)cyclopentyl]-4-heptenoic acid, hydrochloride Method a)

A solution of Intermediate 25 (0.125 g) in ethanol (15 ml) and 2N NaOH (5 ml) was heated under reflux for 5 h. The cooled solution was diluted with pH 6.5 phosphate buffer (75 ml) and extracted with $CH_2Cl_2$ (3×40 ml). The combined extracts were shaken thoroughly with 2N hydrochloric acid then dried and evaporated. The residue was triturated with ER to give the title compound (0.1 g), m.p. 66°-67°.

$[\alpha]_D^{22.8} = +57.6°$ ($CHCl_3$).

T.l.c. 4:1 EA-methanol Rf 0.28.

Method b)

A solution of Intermediate 20e (0.665 g) in acetone (45 ml) and 2N hydrochloric acid (5 ml) was kept at ambient temperature for 18 h. The acetone was removed in vacuo and the residue in water (75 ml) was extracted with ER (2×50 ml, discarded). The aqueous layer was extracted with $CH_2Cl_2$ (3×50 ml) and the combined extracts were dried and evaporated to give an oil. Trituration with ER gave the title compound as a solid (0.4 g), m.p. 66°-67°.

$[\alpha]_D^{23.5} = +58°$ ($CHCl_3$).

T.l.c. Identical mixed spot with the product of method a.

We claim:

1. In a process for the preparation of a compound of formula (1):

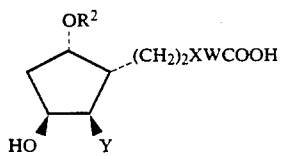

(1)

wherein

W is straight or branched $C_{1-7}$ alkylene;

X is cis or trans —CH=CH—;

Y is a saturated heterocyclic amino group (attached to the cyclopentane ring via the nitrogen atom) selected from (1) pyrrolidino, piperidino, morpholino, piperazino, thiamorpholino, 1,1-dioxothiamorpholino, hexamethyleneimino, or (b) pyrrolidino, piperidino, morpholino, piperazino, thiamorpholino, 1,1-dioxothiamorpholino, hexamethyleneimino which is substituted by one or more $C_{1-4}$ alkyl groups; and $R^2$ is (i) straight or branched $C_{1-5}$ alkyl substituted by (a) phenyl or phenyl substituted by $C_{1-6}$ alkyl, $C_{5-7}$ cycloalkyl, phenylalkyl having a $C_{1-3}$ alkyl portion, thienyl, phenyl or phenyl substituted by $C_{1-4}$ alkyl, $C_{1-4}$ alkoxy or phenyl, (b) thienyl or thienyl substituted by $C_{1-6}$ alkyl, $C_{1-6}$ alkoxy, $C_{5-7}$ cycloalkyl, phenyl or phenyl substituted by $C_{1-3}$ alkyl, $C_{1-3}$ alkoxy or halogen, or (c) naphthyl or naphthyl substituted by $C_{1-4}$ alkyl or $C_{1-4}$ alkoxy, or (ii) cinnamyl, or a physiologically acceptable salt or solvate thereof wherein the improvement comprises a one pot reduction and hydrolysis of a compound of formula (3):

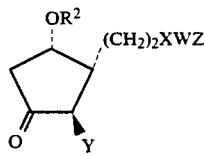

(3)

without a separate hydrolysis step;

where $R^2$, Y, X and W are defined above and Z is —$CO_2R^1$ where $R^1$ is (1) —$CR^4R^5R^6$ in which $R^4$ and $R^5$ are each phenyl or phenyl substituted by $C_{1-4}$ alkyl, $C_{1-4}$ alkoxy, di-($C_{1-4}$) alkylamino, nitro or halogen and $R^6$ is a hydrogen atom or a substituted or unsubstituted phenyl group as defined for $R^4$ and $R^5$, (2) —$SiR^7R^8R^9$ where $R^7$, $R^8$ and $R^9$ are aryl or $C_{1-6}$ alkyl, (3) —$CH_2CCl_3$ (4) —$CH_2BCH_2R^{11}$ where B is —O— or —S—, and $R^{11}$ is H or $C^{1-4}$ alkyl to produce a compound of formula (1);

said reduction being carried out with a selective reducing agent for converting the ring oxo group into the ring β hydroxy group; and said hydrolysis being effected with an inorganic base or an organic or inorganic acid.

2. The process of claim 1 further comprising after the formation of the compound of formula (1), performing one or more of the following conversions:
 (i) liberating the free acid of formula (1) from a salt initially formed,
 (ii) converting one salt of formula (1) into another, or
 (iii) treating a compound of formula (1) with an acid or a base to form a salt.

3. A process as claimed in claim 1 wherein $R^1$ is a group of the type (1).

4. A process as claimed in claim 2 wherein $R^1$ is a group of the type (1).

5. A process as claimed in claim 1 wherein $R^1$ is triphenylmethyl.

6. A process as claimed in claim 2 wherein $R^1$ is triphenylmethyl.

7. A process as claimed in claim 1 wherein the hydrolysis is effected with hydrochloric acid.

8. A process as claimed in claim 2 wherein the hydrolysis is effected with hydrochloric acid.

9. A process as claimed in claim 1 wherein the compound of formula (1) produced is isolated in the form of a salt.

10. A process as claimed in claim 2 wherein the compound of formula (1) produced is isolated in the form of a salt.

11. A process as claimed in claim 1 wherein the hydrolysis is effected with hydrochloric acid and the compound of formula (1) is isolated as its hydrochloride salt.

12. A process as claimed in claim 2 wherein the hydrolysis is effected with hydrochloric acid and the compound of formula (1) is isolated as its hydrochloride salt.

13. A process as claimed in claim 1 wherein W is —$CH_2CH_2$—, X is cis —CH=CH—, Y is morpholino or piperidino, and $R^2$ is benzyl in which the phenyl group is substituted by phenyl, tolyl or methoxyphenyl.

14. A process as claimed in claim 2 wherein W is —$CH_2CH_2$—, X is cis —CH=CH—, Y is morpholino or piperidino, and $R^2$ is benzyl in which the phenyl group is substituted by phenyl, tolyl or methoxylphenyl.

15. A process as claimed in claim 13 wherein the compound produced is [1R-[1α(Z),2β,3β,5α]]-(+)-7-[5-[(1,1'-biphenyl)-4-yl]methoxyl]-3-hydroxy-2-(1-[piperidinyl) cyclopentyl]-4-heptonoic acid hydrochloride.

16. A process as claimed in claim 14 wherein the compound produced is [1R-[1α(Z),2β,3β,5α]]-(+)-7-[5-[(1,1'-biphenyl)-4-yl]methoxyl]-3-hydroxy-2-(1-[piperidinyl) cyclopentyl]-4-heptonoic acid hydrochloride.

17. The method of claim 1 wherein the selective reducing agent is selected from the group consisting of dibutylaluminium-2,6-di-t-butyl-4-methylphenoxide, lithium trisiamylborohydride, 2,6-di-tert-butyl-4-methylphenoxymagnesium hydride, potassium tri-isopropoxyborohydride, and tri-isobutylaluminium.

18. The method of claim 17 wherein the one pot reduction and hydrolysis procedure is conducted at a temperature range of −65° C. to about room temperature.

* * * * *